(12) United States Patent
Teague et al.

(10) Patent No.: US 10,636,517 B1
(45) Date of Patent: Apr. 28, 2020

(54) COMPUTER-EXECUTABLE APPLICATION THAT FACILITATES PROVISION OF A COLLABORATIVE SUMMARY FOR A CARE PLAN

(71) Applicant: Allscripts Software, LLC, Raleigh, NC (US)

(72) Inventors: Ross C. Teague, Cary, NC (US); Gary S. Gartner, Durham, NC (US)

(73) Assignee: ALLSCRIPTS SOFTWARE, LLC, Raleigh, NC (US)

( * ) Notice: Subject to any disclaimer, the term of this patent is extended or adjusted under 35 U.S.C. 154(b) by 355 days.

(21) Appl. No.: 15/385,646

(22) Filed: Dec. 20, 2016

(51) Int. Cl.
- *G16H 10/60* (2018.01)
- *H04L 29/06* (2006.01)
- *G16H 40/63* (2018.01)

(52) U.S. Cl.
CPC ............ *G16H 10/60* (2018.01); *G16H 40/63* (2018.01); *H04L 67/42* (2013.01)

(58) Field of Classification Search
None
See application file for complete search history.

(56) References Cited

U.S. PATENT DOCUMENTS

| | | | | |
|---|---|---|---|---|
| 2006/0281977 | A1* | 12/2006 | Soppet | G06F 19/3481 600/300 |
| 2011/0218814 | A1* | 9/2011 | Coats | G06Q 50/22 705/2 |
| 2011/0225003 | A1* | 9/2011 | McCallie, Jr. | G06Q 10/10 705/2 |
| 2011/0301982 | A1* | 12/2011 | Green, Jr. | G06Q 10/06 705/3 |
| 2012/0116800 | A1* | 5/2012 | McCallie | G06Q 10/10 705/2 |
| 2013/0041677 | A1* | 2/2013 | Nusimow | G06Q 50/22 705/2 |
| 2014/0033028 | A1* | 1/2014 | Tatiyants | G06F 17/24 715/256 |
| 2015/0213222 | A1* | 7/2015 | Amarasingham | G16H 50/30 705/2 |
| 2015/0254429 | A1* | 9/2015 | Belcher | G06Q 50/22 705/3 |
| 2015/0324525 | A1* | 11/2015 | Saffran | G16H 10/60 705/3 |
| 2017/0076046 | A1* | 3/2017 | Barnes | G06F 19/321 |

* cited by examiner

*Primary Examiner* — Michael Tomaszewski
*Assistant Examiner* — Jay M. Patel
(74) *Attorney, Agent, or Firm* — Medley, Behrens & Lewis, LLC (57) ABSTRACT

Described herein are technologies related to a care plan application that is configured to provide a collaborative summary field to client computing devices operated by healthcare workers who partake in a care plan for a patient. The collaborative summary field is usable to set forth freeform text and/or modify freeform text, such that a collaborative summary depicted in the collaborative summary field alters over time. Further, each healthcare worker who has access to the care plan is authorized to update the collaborative summary.

18 Claims, 7 Drawing Sheets

COMPUTER-EXECUTABLE APPLICATION THAT FACILITATES PROVISION OF A COLLABORATIVE SUMMARY FOR A CARE PLAN

BACKGROUND

Electronic health record applications (EHRs) are robust computer-executable applications utilized by healthcare enterprises in connection with providing care to patients. An EHR, for example, can be configured to perform tasks related to patient intake, prescribing medication, assisting with diagnosis, and so forth. The EHR stores and retrieves data to and from a backend database. It can be ascertained that a healthcare worker utilizing an EHR can retrieve a significant amount of data about a patient from the database. Conventionally, however, records retained in such database tend to be data-entry specific, and accordingly the data fails to provide an overall summarization regarding the health and/or personality of the patient. In other words, for a clinician to acquire a high-level summary about the health of the patient, the clinician may first navigate to a page provided by the EHR that is configured to provide family history data. After reviewing the family history data, the clinician may navigate to a page provided by the EHR that is configured to present current prescriptions for the patient. To obtain summary-level data about the patient, then, the clinician must navigate to several different pages, which is time-consuming and is an inefficient use of computer resources.

This problem is exacerbated when the clinician is part of a care team for the patient (where the care team is tasked with helping the patient adhere to a care plan). More specifically, a care plan for a patient describes health problems experienced by the patient, diagnoses pertaining to the patient, tasks that are to be performed by the clinicians and/or a healthcare worker to address the problems, goals for the patient over time, information as to status of the patient with respect to the goals, etc. Typically, multiple clinicians with different fields of expertise may partake in the care plan for the patient, particularly when the health of the patient is somewhat complex. Recently, computer-executable care plan applications have been developed, wherein clinicians partaking in a care plan for a patient can be provided with electronic access to the care plan. The development of care plan applications is enabled by health-related data about patients becoming more readily accessible in population data. For instance, health information exchanges (HIEs) expose at least some health-related data of EHRs, wherein exposed data can be retrieved by other computer-executable applications.

While this data can be valuable to a care plan application, the care plan application suffers even more so than EHRs with respect to overload of data. In other words, when a healthcare worker partaking in a care plan for the patient opens the care plan application, conventionally, the healthcare worker must hunt and search for information about what has happened with respect to the patient since the healthcare worker last met with the patient. Moreover, conventional care plan applications fail to provide an efficient mechanism that allows for a healthcare worker to retrieve insights about the patient from other healthcare workers partaking in the care plan. The above-described hunting for information consumes a significant amount of time, and can lead to an incomplete understanding of the patient (particularly with respect to how the patient is progressing in the care plan).

SUMMARY

The following is a brief summary of subject matter that is described in greater detail herein. This summary is not intended to be limiting as to the scope of the claims.

Various technologies pertaining to a computer-executable care plan application are described herein, where the care plan application is configured with a collaborative summary module, wherein the collaborative summary module is configured to provide a collaborative summary section to client computing devices of healthcare workers partaking in a care plan for a patient. The collaborative summary section is configured to display freeform text set forth by healthcare workers partaking in the care plan, where the freeform text is editable by any healthcare worker partaking in the care plan. Hence, clinicians partaking in the care plan for the patient can provide summary information about the patient that may be relevant to other members of the care team. For instance, in the collaborative summary, a healthcare worker can leave comments for themselves and for others on the care team, such that the collaborative summary can provide an up-to-date synopsis. In other words, the collaborative summary can present, to each healthcare worker on the care team, a relevant clinical summary that can evolve as the care plan for the patient changes over time. The collaborative summary can be edited by any member of the care team who has access to the care plan by way of the care plan application, such that the collaborative summary leverages how healthcare workers speak with each other in a narrative clinical summary fashion. Thus, the care plan application provides a tool for care team members that allow the care team members to create and consume a collaborative summary pertaining to the care plan, which can act as the "glue" that binds together parameters of the care plan (problems, goals, medications, allergies, immunizations, etc.), and further binds together information available to clinicians about the patient.

The care plan application, therefore, solves a problem associated with conventional care plan applications, as conventionally, a care plan application can provide information about a care plan to healthcare workers on a care team working with the care plan; however, the conventional care plan application fails to provide a mechanism that allows a healthcare worker to generate or consume a summary pertaining to the patient and how the patient has progressed in the care plan. For instance, a healthcare worker may have an upcoming appointment with a patient, where it may have been a long time since the healthcare worker last saw the patient. The healthcare worker may wish to quickly get up to speed on what has happened with the patient, e.g. the healthcare worker may want to know what treatment other healthcare workers partaking in the care plan have tried in the past (i.e., what treatments worked, what treatments did not work, why certain decisions were made, etc.). The care plan application described herein provides a tool that allows healthcare workers partaking in the care plan to set forth this type of information in a collaborative summary, such that the healthcare worker can have the benefit of knowing what has motivated the patient to change behaviors in the past. Again comparing conventional care plan applications with the care plan application described herein, conventionally, for the healthcare worker to acquire this information, the healthcare worker would have to leave the care plan application and piece together relevant information to create a high-level summary in the mind of the healthcare worker, which can consume a lot of time and lead to an incomplete or potentially inaccurate patient summary. As noted above, the care plan application described herein solves this problem by providing a tool that allows healthcare workers on the care team to create, consume, and edit a collaborative summary about the care plan of the patient.

An exemplary operation of the care plan application is now set forth. A healthcare worker may be scheduled to see a patient, and knowing that the patient is on the schedule and that the healthcare worker is on a care team for the patient, the healthcare worker can initiate a care plan application, which maintains a care plan for the patient. The care plan can include, for example, identities of other healthcare workers on the care team, diagnosed diseases of the patient, problems that are to be addressed in the care plan, identities of clinicians who are tasked with assisting the patient in addressing the problems, treatments being performed to address such problems, goals for the patient, time that the patient is to achieve the goals, etc. As indicated previously, however, this information, collectively, may be overwhelming to the healthcare worker, and is somewhat incomplete (as it does not relay insights that other healthcare workers on the care team may have about the patient). The care plan application provides a tool that allows the healthcare worker to retrieve a collaborative summary about the care plan for the patient, wherein the collaborative summary may include freeform text previously set forth by the healthcare worker or other healthcare workers on the care team.

For instance, the healthcare worker can select a button in a graphical user interface of the care plan application, wherein the care plan application, responsive to the button being selected by the healthcare worker, presents a collaborative summary field on a display of the computing device operated by the healthcare worker. The collaborative summary field comprises, for example, a collaborative summary that includes editable freeform text, where the text can include summary information generated by other healthcare workers partaking in the care plan. It can, therefore, be ascertained that the collaborative summary can include notes from healthcare workers that describe treatments that have been attempted in the past, as well as information as to what treatments worked or were discontinued, as well as what motivated the patient to reach a goal. The collaborative summary field can also depict version and history information for the collaborative summary, so that the healthcare worker can identify other healthcare workers who have modified the collaborative summary and when such modifications were made. The healthcare worker can update the collaborative summary to identify treatments or conditions that should be emphasized when other healthcare workers are assisting the patient with reaching goals in the care plan. Yet another benefit of the collaborative summary is that the healthcare worker need not leave the page that depicts the care plan for the patient and go searching through, for example, EHR records for information that is relevant to the patient; hence, the care plan application that provides the collaborative summary results in computing resources being more efficiently utilized when compared to resource usage of conventional care plan applications.

The healthcare worker may then utilize the information in the collaborative summary in connection with providing care to the patient. Based upon the experience of the healthcare worker with the patient, the healthcare worker may choose to update the collaborative summary in the collaborative summary field. For instance, the healthcare worker can ascertain, through a conversation with the patient, that the patient is highly motivated to appear physically fit for a high school reunion that is scheduled to occur in four months. The healthcare worker may then update the collaborative summary such that other healthcare workers on the care team can be informed of the motivation of the patient, thereby assisting the other healthcare workers in helping the patient to meet his or her goals in the care plan.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

DETAILED DESCRIPTION

Various technologies pertaining to a care plan application that is configured to provide an editable care plan summary to healthcare workers who are part of a care team for a patient are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Further, as used herein, the terms "component" and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices. Further, as used herein, the term "exemplary" is intended to mean serving as an illustration or example of something, and is not intended to indicate a preference.

Described herein are various technologies pertaining to a computer-executable care plan application that is configured to allow healthcare workers who partake in a care plan for a patient to retrieve, create, and/or edit a collaborative summary for the care plan. The care plan for the patient defines problems of the patient that are to be addressed by a care team (the healthcare workers who partake in the care plan), techniques recommended by the healthcare workers to address the problems, and goals for the patient with respect to the problems. Oftentimes, particularly for a patient that has complex health issues, a care plan for the patient may include several problems, wherein several different healthcare workers (who may be practicing at several different health facilities) are tasked with assisting the patient in reaching the goals defined in the care plan. The care plan application described herein can provide access to the care plan for the patient to all members of the care team. Conventionally, a care team member can open a care plan application and review the care plan for the patient. The care plan application sets forth identities of the healthcare workers on the care team, the problems being addressed in the care plan, diagnoses, etc., wherein this information is typically generated by different health care workers identified in the care plan.

Oftentimes, information in the care plan is retrieved from an EHR, wherein a healthcare worker on the care team utilizes a "copy and forward" command to extract data from the EHR and place the data in the care plan. This information tends to be full of medical jargon and often fails to provide an effective overview of the care being provided to the patient by the healthcare worker. To address this problem, the care plan application, as will be described in greater detail below, causes a collaborative summary field to be presented in a graphical user interface (GUI) of the care plan application. The collaborative summary field is configured as a text display and entry field, such that any healthcare worker who is on the care team for the patient can set forth freeform text in the collaborative summary field, thereby allowing each healthcare worker on the care team to provide insightful summary-type information in the collaborative summary. Further, each healthcare worker can update the collaborative summary; hence, over time, the collaborative summary field can present a robust collaborative summary pertaining to the care provided by the patient with respect to the care plan.

Figure 1:
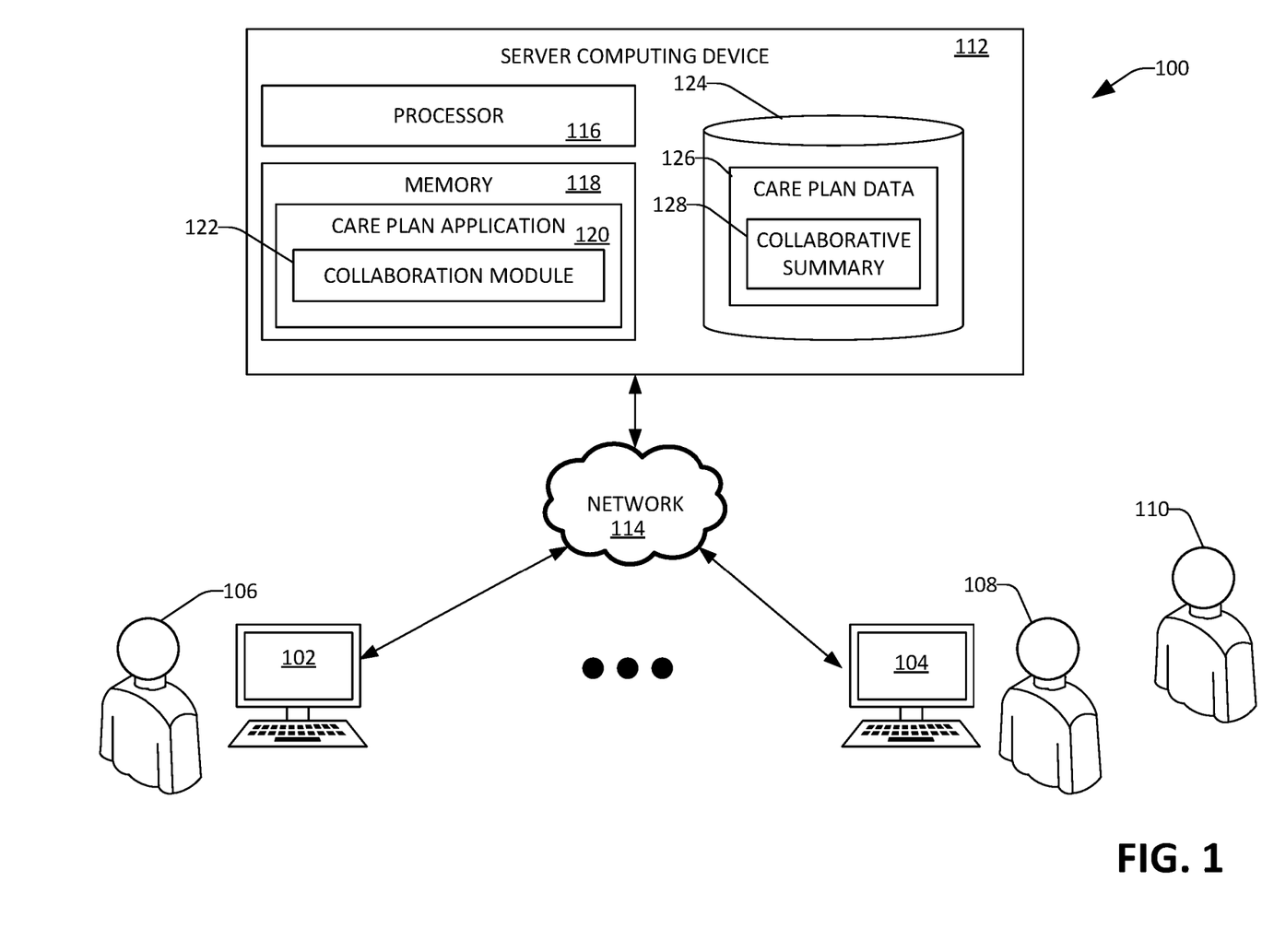
FIG. 1 is a functional block diagram of an exemplary system that facilitates provision of an editable collaborative summary to a healthcare worker by way of a computer-executable care plan application.

With reference now to FIG. 1, an exemplary system 100 that facilitates creation, retrieval, and editing of a collaborative summary for a care plan of a patient is illustrated. The system 100 includes a plurality of client computing devices 102-104 that are respectively operated by healthcare workers 106-108 who are members of a care team for a patient 110. Each client computing devices 102-104 may be any suitable type of client computing device including, but not limited to, a desktop computing device, a mobile telephone, a tablet computing device, a laptop computing device, a wearable computing device, or the like.

The system 100 also comprises a server computing device 112 that is in communication with the client computing devices 102-104 by way a network 114. The server computing device 112 includes a processor 116 and memory 118, wherein the memory 118 stores instructions that are executed by the processor 116. More specifically, the memory 118 can have a care plan application 120 loaded therein that is executed by the processor 116. The care plan application 120 is configured to create and maintain an electronic care plan for the patient 110. As will be understood by one skilled in the art, a care plan for the patient 110 can include diagnoses of diseases and/or identities of health conditions of the patient 110, a list of problems that is to be addressed in the care plan (e.g., the patient 110 is overweight, the patient 110 has discomfort in his feet, etc.), identities of healthcare workers on the care team of the patient 110 are tasked with addressing the respective problems identified in the care plan, treatments recommended by the healthcare workers to help the patient 110 address the problems, goals for the patient 110 with respect to the identified problems (e.g., lose 20 pounds, be able to walk a mile without extreme discomfort, etc.), target dates for reaching the goals, and so forth.

While not shown, the care plan application 120 can be in direct or indirect communication with electronic health record applications (EHRs) utilized by the healthcare workers 106-108 on the care team for the patient 110. For example, the clinician 106 operating the client computing device 102 may utilize an EHR when providing care to the patient 110, and may input data to the EHR pertaining to medication that is being prescribed by the healthcare worker 106 to the patient 110. The care plan application 120 can update the care plan for the patient 110 based upon content in the EHR (e.g., the care plan application 120 can pull data from the EHR, the EHR can push data to the care plan application 120, a health information exchange (HIE) may make data from the EHR available to the care plan application 120, etc.). In an example, the care plan application 120 can update the care plan for the patient 110 to indicate that a treatment for the patient 110 set forth by the healthcare worker 106 includes the patient 110 taking the medication prescribed by the healthcare worker 106. Thus, the care plan application 120 may automatically or semi-automatically update the care plan based upon interactions of the healthcare workers 106-108 with respective EHRs.

The care plan application 120 also includes a collaboration module 122 that facilitates creation of a collaborative summary for the care plan of the patient 110, editing of the collaborative summary, and/or provision of the collaborative summary to the client computing devices 102-104 operated by the healthcare workers 106-108. Briefly, the collaboration module 122 causes a collaborative summary field to be presented on the client computing devices 102-104 when applications (not shown) on the client computing devices 102-104 are in communication with the care plan application 120. The collaborative summary field is a text entry and editing field, such that each of the healthcare workers 106-108 can review freeform text in the collaborative summary field, generate new freeform text in the collaborative summary field, and/or update existing text in the collaborative summary field. In other words, freeform text in the collaborative summary field is reviewable by all healthcare workers on the care team of the patient 110 and is editable by all healthcare workers on the care team of the patient 110. The collaborative summary field, then, allows the healthcare workers 106-108 to set forth notes to themselves or other healthcare workers on the care team, where the notes may include insights pertaining to the patient 110, description of previous treatments attempted with the patient 110 and their outcomes, etc., wherein this type of information would otherwise be unavailable to the healthcare workers 106-108. Hence, a healthcare worker on the care team for the patient 110, by text in the collaborative summary field, can quickly ascertain a high-level summary about care of the patient 110 that has been collaboratively generated by members of the care team for the patient 110.

The server computing device 112 also includes a data repository 124 that stores care plan data 126. The care plan data 126 may include the electronic care plan referenced above, as well as a collaborative summary 128 that has been collaboratively generated by the healthcare workers 106-108 way of the collaboration module 122. When the collaboration module 122 first receives freeform text to be included in a collaborative summary for the patient 110, the collaboration module 122 can cause the collaborative summary 128 for the patient 110 to be included in the care plan data 126 for the patient 110. Subsequently, when a request is received for the collaborative summary 128, the collaboration module 122 can retrieve the collaborative summary 128 from the data repository 124 and cause the server computing device 112 to transmit the collaborative summary 128 to the client computing device from which the request was received. Further, as will be described in greater detail herein, the collaboration module 122 can maintain an update log, such that updates to the collaborative summary 128 are tracked over time. This allows for the collaboration module 122 to present healthcare workers with versioning information for the collaborative summary 128, history of alterations made to the collaborative summary 128, identities of healthcare workers who updated the collaborative summary 128, and so forth.

Exemplary operation of the system 100 is now set forth. In an example, the healthcare worker 106 may be the primary care physician (PCP) for the patient 110. The healthcare worker 106 can ascertain that the patient 110 has several problematic health conditions, and accordingly the healthcare worker 106 can construct a care plan for the patient 110 (potentially with the assistance of other healthcare workers). To create the care plan, the healthcare worker 106 can cause the client computing device 102 to execute a client-side application that communicates with the care plan application 120 executing on the server computing device 112, and can set forth input to the client-side application that causes the care plan application 120 to construct a care plan for the patient 110. In doing so, the healthcare worker 106, for example, can indicate that the healthcare worker 108 is to be included in the care team and, subsequently, the healthcare worker 106, healthcare worker 108, and other members of the care team can collaborate to update the care plan for the patient 110 by way of the care plan application 120. As noted previously, the care plan may include diagnoses, problems that are to be addressed, roles of the healthcare workers 106-108 with respect to the problems, treatments recommended to address the problems, goals for the patient 110, and so forth.

As the healthcare worker 106 is the PCP for the patient 110, the healthcare worker 106 may have insight about the personality of the patient 110, family history of the patient 110, information as to what motivates the patient, etc. Conventionally, there has been no suitable mechanism for the healthcare worker 106 to effectively share this knowledge with other healthcare workers partaking in the care plan for the patient 110. As noted above, however, the care plan application 120 includes the collaboration module 122, which provides a mechanism (a collaborative summary field) for the healthcare worker 106 to set forth freeform text that is reviewable and editable by any healthcare worker who is authorized to access the care plan by way of the care plan application 120.

For example, responsive to receipt of authentication data from the healthcare worker 106, the client-side application on the client computing device 102 can transmit a request for the care plan of the patient 110 to the care plan application 120. The client-side application may be a browser, a client side application that is dedicated to the care plan application 120, etc. The care plan application 120, responsive to receiving the request, causes the server computing device 112 to transmit the care plan of the patient 110 to the client computing device 102.

The client computing device 102 displays the care plan for the patient 110 on the display thereof. The client computing device 102 can receive input from the healthcare worker 106 that indicates that the healthcare worker 106 intends to generate or update a collaborative summary pertaining to the care plan of the patient 110. For example, a graphical user interface for the care plan application 120 may include a button that, when selected, causes the collaborative summary field to be presented on the display of the client computing device 102. The client computing device 102 may then receive text input from the healthcare worker 106, such that the collaborative summary field is populated with freeform text. For example, the freeform text may be received by way of a keyboard, voice-to-text input, or the like. The client computing device 102, responsive to receiving the freeform text, can transmit this freeform text to the server computing device 112, whereupon it is provided to the care plan application 120. The collaboration module 122 can update the care plan data 126 to include the collaborative summary 128, wherein the collaborative summary 128 comprises the freeform text set forth by the healthcare worker 106, an identity of the healthcare worker 106, and a time that the freeform text was received by the care plan application 120.

Later, the patient 110 may have an appointment with the healthcare worker 108, wherein (as noted above) the healthcare worker 108 is a part of the care team for the patient 110. Prior to the appointment or at the time of the appointment, the client computing device 104 can executed a client-side application (not shown) that communicates with the care plan application 120, and the client-side application (responsive to receipt of input from the healthcare worker 108) can transmit a request for the care plan to the care plan application 120. Responsive to receiving the request, the care plan application 120 causes the server computing device 112 to transmit the care plan to the client computing device 104, whereupon the care plan is displayed on the display of the client computing device 104 (e.g., in a GUI for the care plan application 120). The GUI can include a badge of other notification that indicates that the collaborative summary 128 exists for the care plan.

The client computing device 104 can receive input that indicates that the healthcare worker 108 wishes to review the collaborative summary 128, and the client computing device transmits a request to the server computing device 112 for the care plan summary 128. The collaboration module 122 can receive the request, and (responsive to receipt of the request) searches over content of the data repository 124 for the collaborative summary 128. The collaboration module 122 retrieves the collaborative summary 128 from the care plan data 126, and causes the server computing device 112 to transmit the collaborative summary 128 to the client computing device 104. The collaborative summary 128 is presented in the collaborative summary field, and the healthcare worker 108 can review the collaborative summary, thereby quickly acquiring information about the patient 110 that the healthcare worker 108 would otherwise be unable to acquire or would take a large amount of time to acquire. During the appointment, the healthcare worker 108 interacts with the patient 110, whereupon the healthcare worker 108 obtains new insights as to how to provide the best care possible for the patient 110. These insights may include reasons why the healthcare worker 108 has recommended certain treatment, information as to what appears to be motivating the patient 110, and the like. In another example, the healthcare worker 108 may acquire updated information from the patient 110 compared to the information that the healthcare worker 106 had when initially generating the collaborative summary 128. Accordingly, the healthcare worker 108 has the option of appending new freeform text to the collaborative summary 128 and/or editing the freeform text previously set forth by the healthcare worker 106.

The client computing device 104, responsive to receiving input as to an update to the collaborative summary 128, can transmit the update to the server computing device 112, whereupon it is received by the collaboration module 122. The collaboration module 122 can update a change log for the collaborative summary 128, wherein the change log can identify portions of the collaborative summary 128 that were updated by the healthcare worker 108, can identify that it was the healthcare worker 108 who set forth the update, and can further identify a time of the update. In other words, the collaboration module 122 causes versioning and history information about the collaborative summary 128 to be retained in the care plan data 126.

Continuing with the example, the patient 110 may have a subsequent appointment with the healthcare worker 106, wherein the appointment is scheduled to further assist the patient 110 in reaching a goal in the care plan. Prior to the appointment or at the time of the appointment, the client computing device 102 can be operated by the healthcare worker 106 to transmit a request for the care plan to the server computing device 112. The server computing device 112 receives the request, whereupon the request is provided to the care plan application 120. The care plan application 120, responsive to receiving request, causes the care plan for the patient 110 to be transmitted to the client computing device 102, where it can be reviewed by the healthcare worker 106. The client computing device 102 can receive input from the healthcare worker 106 that indicates that the healthcare worker 106 wishes to review the collaborative summary 128 for the care plan. The client computing device 102, responsive to receiving this input, transmits a request to the server computing device 112 for the collaborative summary 128, whereupon it is provided to the collaboration module 122. The collaboration module 122 retrieves the collaborative summary 128 from the data repository 124 based upon the request, and causes the server computing device 112 to transmit the collaborative summary 128 to the client computing device 102. Responsive to receiving the collaborative summary 129, the client computing device 102 presents the collaborative summary in the collaborative summary field. The healthcare worker 106 can then review the collaborative summary 128 (which includes the new information provided by the healthcare worker 108), thereby allowing the healthcare worker 106 to make better informed decisions about the care of the patient 110. Further, the healthcare worker 106 is able to set forth additional freeform text or other updates to the collaborative summary 128, such that the collaborative summary 128 can change over time as the patient 110 moves towards reaching the goals set forth in the care plan.

As described above, the care plan application 120 may be in communication with one or more EHRs utilized by one or more of the healthcare workers 106-108. Accordingly, the care plan application 120, in an example, can allow an EHR to retrieve the collaborative summary 128 for a patient. For instance, at the point of care, a healthcare worker may interact with an EHR to assist the healthcare worker in providing care to the patient 110. The EHR can pull the collaborative summary 128 from the care plan application 120, such that the collaborative summary 128 can be presented as a note in the EHR. Moreover, while the care plan application 120 is depicted as being a standalone application, in another exemplary embodiment, the care plan application 120 may be a module of an EHR.

Figure 2:
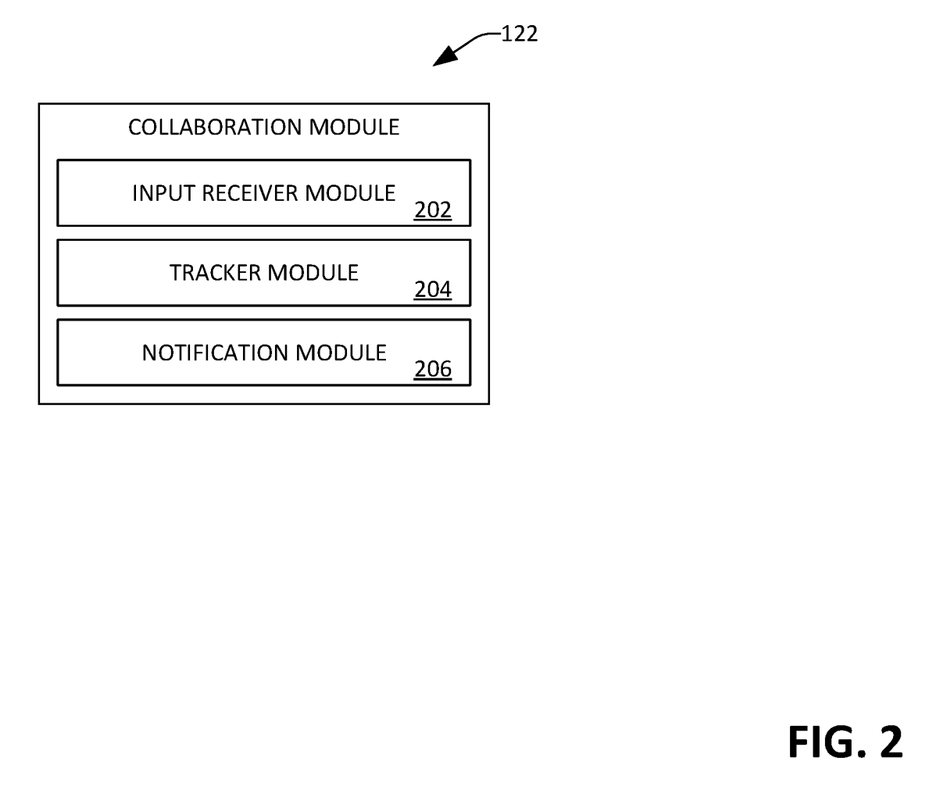
FIG. 2 is a schematic that illustrates an exemplary collaboration module of a care plan application.

Now referring to FIG. 2, a functional block diagram of the collaboration module 122 is illustrated. The collaboration module 122 comprises an input receiver module 202. In an exemplary embodiment, the input receiver module 202 can receive a request for a collaborative summary field to be shown on a display of a client computing device. Responsive to receiving such request, the input receiver module 202 can transmit computer-executable code to the client computing device, wherein the computer-executable code, when executed at the client computing device, causes the collaborative summary field to be presented thereon. The collaborative summary field may include freeform text previously set forth by one or more healthcare workers in a care team of a care plan of the patient 110. The input receiver module 202 may then receive input (e.g., new freeform text and/or updates to existing freeform text), and can cause the input to be included in the collaborative summary 128 in the data repository 124.

The collaboration module 122 may also include a tracker module 204 that is configured to update a change log for the collaborative summary 128. For example, the tracker module 204 can track, for each update made to the collaborative summary 128, an identity of the healthcare worker who set forth the update, a time that the update occurred, and the update itself. Therefore, the tracker module 204 can allow for versioning and history to be available with respect to the collaborative summary 128.

The collaboration module 122 may also optionally include a notification module 206. The notification module 206 can be configured to push notifications to client computing devices operated by healthcare workers whenever an update to a collaborative summary for a patient is received. Accordingly, each member of the care team of the patient 110 can be informed when one of the care team members sets forth an update to the collaborative summary 128 for the care plan. The notification may be in the form of a text message, an e-mail, a notification by way of an EHR, a pop-up notification on a mobile telephone, or the like. Additionally or alternatively, the notification module 206 can cause a notification to be presented when a client computing device accesses the care plan application 120 to retrieve a care plan for the patient 110. In such case, the notification can indicate that since the last time that the care plan was reviewed by a healthcare worker, another healthcare worker in the care team for the patient has updated the collaborative summary 128. This may prompt the healthcare worker to review the collaborative summary 128.

Figure 3:
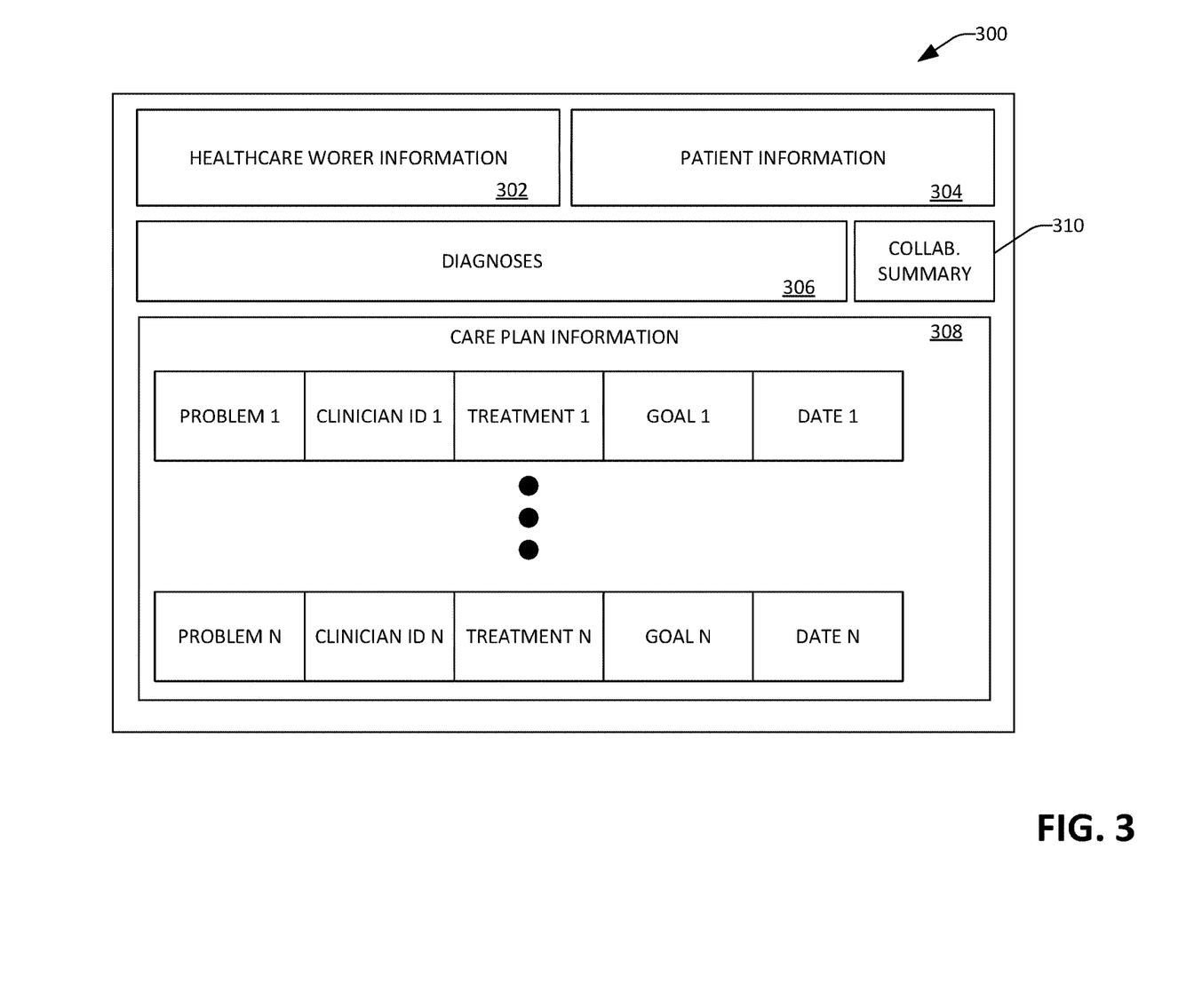
FIG. 3 is a schematic that illustrates an exemplary graphical user interface for a care plan application.

Now referring to FIG. 3, an exemplary GUI 300 for the care plan application 120 is illustrated. The GUI 300 can depict a care plan for the patient 110. The GUI 300 may include a first field 302 that comprises information identifying the healthcare worker that is accessing the care plan of the patient 110. Such information can include the name of the healthcare worker, the role of the healthcare worker in the care plan, and so forth. The GUI 300 may also include a second field 304 that comprises information pertaining to the patient 110. Such information can include patient demographic information, patient name, patient insurance provider, and so forth.

The GUI 300 can include a third field 306 that includes diagnoses for the patient 110. Accordingly, the third field 306 can include identities of diseases with which the patient 110 has been diagnosed. The GUI 300 further includes a fourth field 308 that comprises care plan information. This care plan information, as shown, can include several problems that are to be addressed by way of the care plan. The care plan information may also indicate identities of healthcare workers who are tasked with assisting the patient 110 in addressing the problems. The care plan information may also include treatments recommended by the clinicians to address the problems, as well as goals that the patient 110 is to reach when undertaking the treatments. Finally, the care plan information may include relevant dates, such as when the goals are to be completed, the last time that the patient undertook the treatment, and so forth. Other information may also be included in the care plan.

The GUI 300 may also include a button 310 that, when selected, causes a collaborative summary field to be presented on a display. As indicated previously, the collaborative summary field is a text viewing and text editing field, such that a healthcare worker can create, review, and/or update a collaborative summary for the care plan of the patient 110. While the collaborative summary field has been described as being presented in response to selection of the button 310, in other examples, the collaborative summary field can be presented in response to voice input, can be automatically presented together with the care plan shown in FIG. 3, etc.

Figure 4:
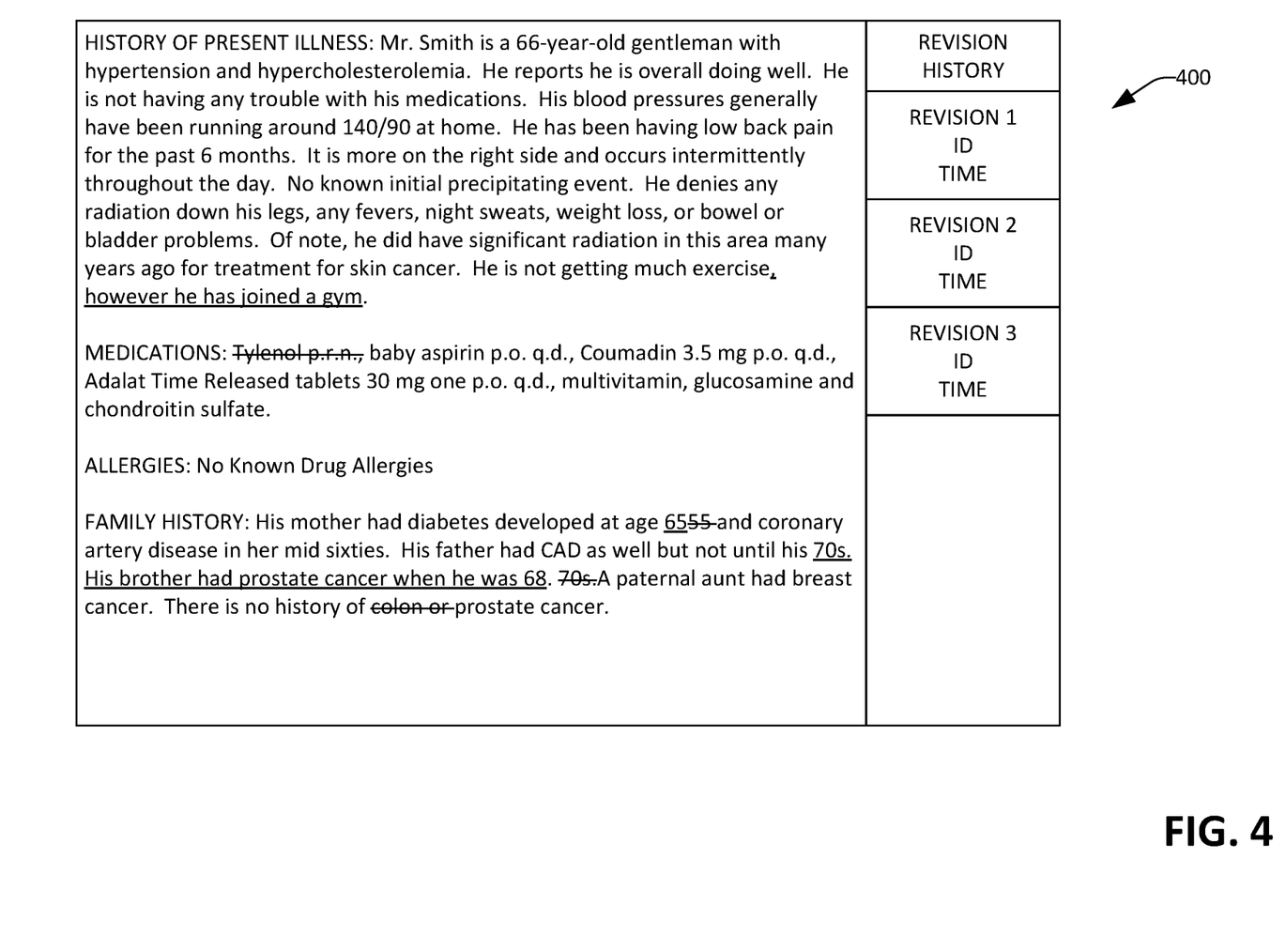
FIG. 4 depicts a graphical user interface of a collaborative summary field.

Turning now to FIG. 4, an exemplary GUI 400 for a collaborative summary field is illustrated. The collaborative summary field includes freeform text that can be reviewed and/or edited (and appended to) by a healthcare worker who is a member of the care team of the patient 110. The collaborative summary field also includes history information that depicts revision history for the collaborative summary 128. The healthcare worker can select a selectable revision history attribute, which causes a version associated with revision history to be presented in the GUI 400. Moreover, the collaborative summary field can depict alterations made to freeform by healthcare workers over time. This can allow a healthcare worker to quickly understand what freeform text has been updated by which healthcare worker on the care team.

Figure 5:
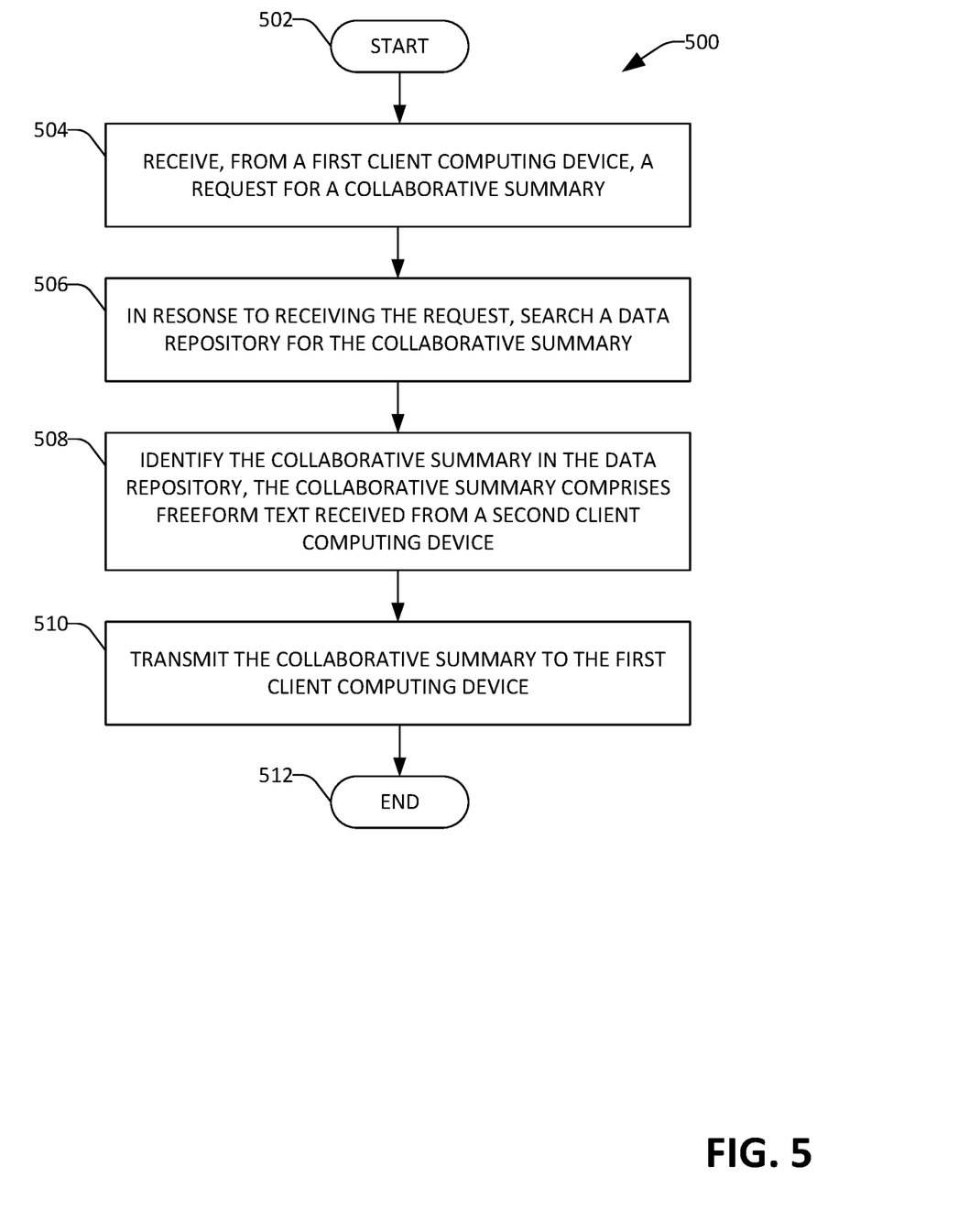
FIG. 5 is a flow diagram that illustrates an exemplary methodology for transmitting a collaborative summary to a client computing device.
Figure 6:
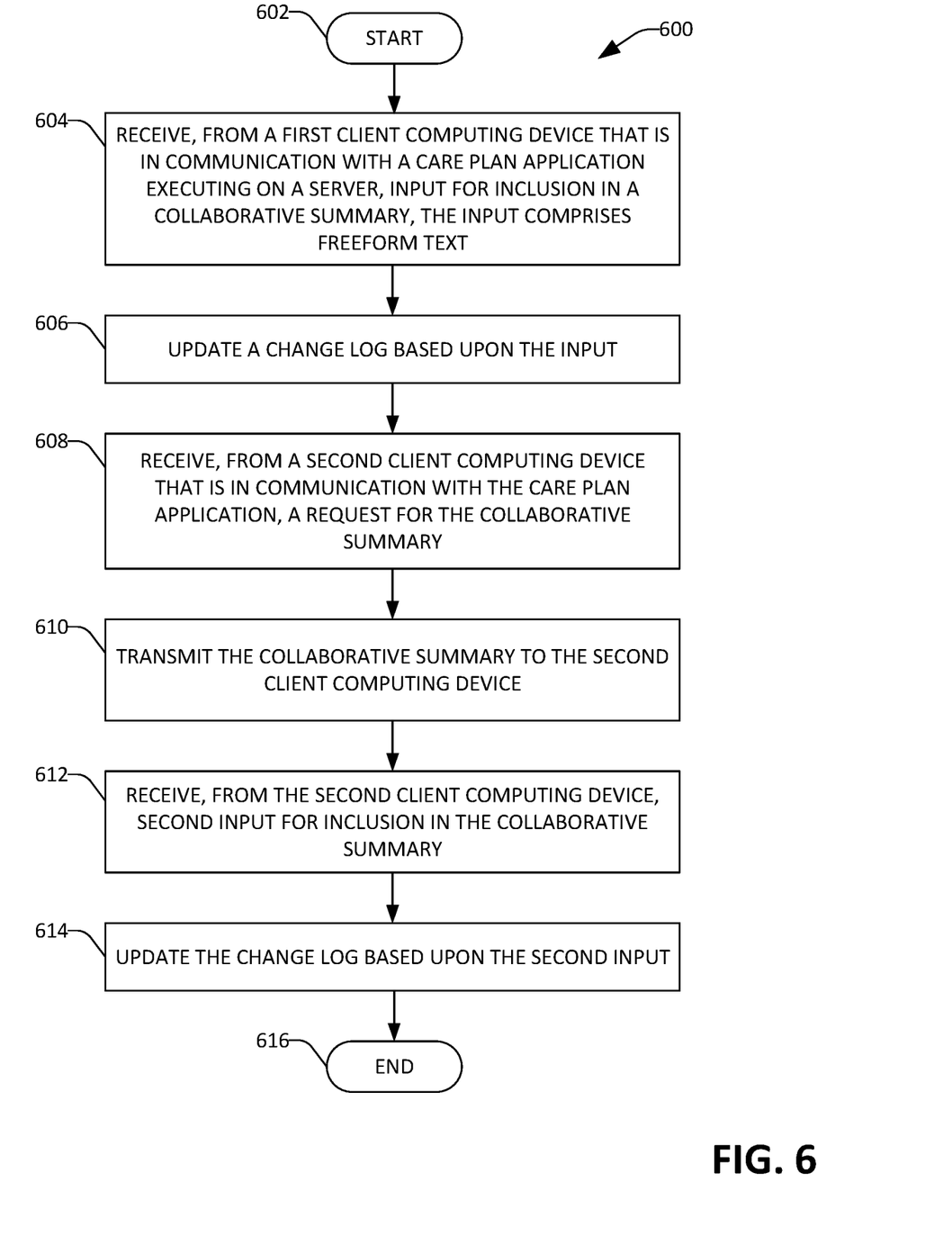
FIG. 6 is a flow diagram that illustrates an exemplary methodology for updating a collaborative summary by way of a care plan application.

FIGS. 5 and 6 illustrate exemplary methodologies relating to a care plan application that facilitates creation, editing, and review of a collaborative summary pertaining to a care plan of a patient. While the methodologies are shown and described as being a series of acts that are performed in a sequence, it is to be understood and appreciated that the methodologies are not limited by the order of the sequence. For example, some acts can occur in a different order than what is described herein. In addition, an act can occur concurrently with another act. Further, in some instances, not all acts may be required to implement a methodology described herein.

Moreover, the acts described herein may be computer-executable instructions that can be implemented by one or more processors and/or stored on a computer-readable medium or media. The computer-executable instructions can include a routine, a sub-routine, programs, a thread of execution, and/or the like. Still further, results of acts of the methodologies can be stored in a computer-readable medium, displayed on a display device, and/or the like.

Referring solely to FIG. 5, an exemplary methodology 500 for transmitting a collaborative summary to a client computing device is illustrated, wherein the methodology 500 is executed by a server computing device. The methodology 500 starts at 502, and at 504 a request for a collaborative summary is received from a first client computing device. For example, the first client computing device can execute an application that interfaces with a care plan application executing on the server computing device. Further, as described above, the request can be initiated responsive to a healthcare worker (who has access to the care plan of the patient) selecting a button in a graphical user interface of the care plan application.

At 506, in response to receiving the request, a data repository is searched for the collaborative summary. The data repository can be searched based upon a care plan ID, based upon a patient ID, and/or based upon a clinician ID. At 508, the collaborative summary is identified in the data repository, wherein the collaborative summary comprises freeform text received from a second client computing device operated by another healthcare worker who has access to the care plan of the patient. At 510, the collaborative summary is transmitted to the first client computing device, whereupon the collaborative summary can be displayed in a collaborative summary field of the GUI of the care plan application. At such time, the healthcare worker operating the first client computing device, can review the collaborative summary, make updates the collaborative summary, etc. The methodology 500 completes at 512.

With reference now to FIG. 6, an exemplary methodology 600 for updating a collaborative summary is illustrated. The methodology 600 can be executed by a server computing device that is in communication with multiple client computing devices operated by healthcare workers who partake in a care plan for a patient. The methodology 600 starts at 602, and at 604 input is received, wherein the input is received from a first client computing device, and further wherein the input is for inclusion in a collaborative summary for a care plan. As described above, the input comprises freeform text set forth by a healthcare worker who partakes in the care plan. At 606, a change log is updated based upon the input. The change log can indicate which portions of the collaborative summary were updated, an identity of the healthcare worker who set forth the update, and a time when the update was made.

At 608, a request for the collaborative summary is received from a second client computing device that is in communication with the care plan application. The second client computing device is operated by a second clinician who partakes in the care plan for the patient. At 610, the collaborative summary is transmitted to the second client computing device responsive to receiving request from the second client computing device. At 612, second input is received from the second client computing device, wherein the second input comprises at least one of a modification to the freeform text existent in the collaborative summary or additional freeform text to be included in the collaborative summary. At 614, the change log is updated based upon the second input. The methodology 600 illustrates that multiple healthcare workers who partake in the care plan for a patient can update and review the collaborative summary, thereby allowing the collaborative summary to change over time as the patient 110 attempts to meet goals in the care plan. The methodology 600 completes at 616.

Figure 7:
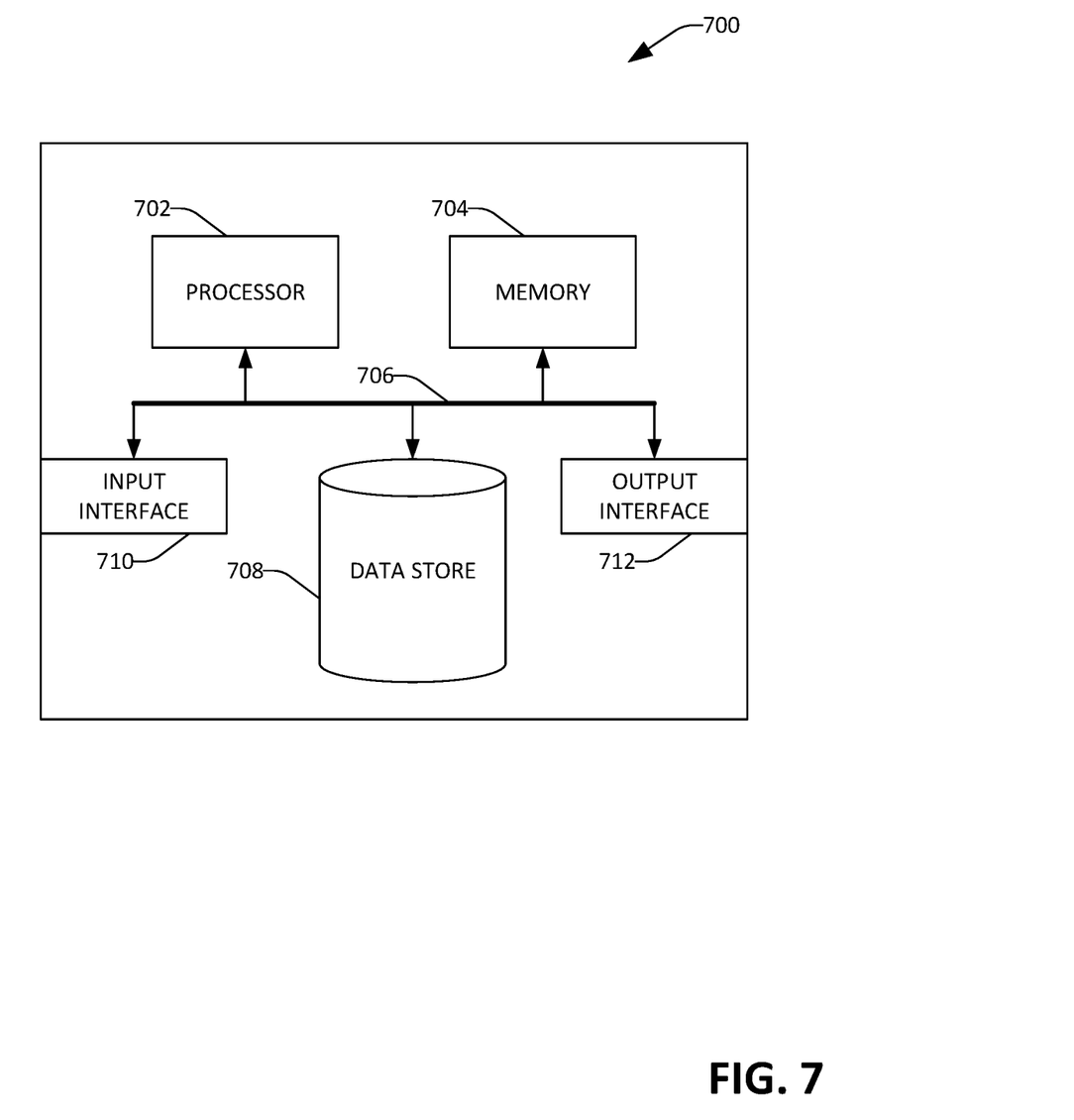
FIG. 7 is an exemplary computing device.

Referring now to FIG. 7, a high-level illustration of an exemplary computing device 700 that can be used in accordance with the systems and methodologies disclosed herein is illustrated. For instance, the computing device 700 may be used in a system that supports creation, editing, and review of a collaborative summary. By way of another example, the computing device 700 can be used in a system that supports provision of a collaborative care plan summary to an EHR. The computing device 700 includes at least one processor 702 that executes instructions that are stored in a memory 704. The instructions may be, for instance, instructions for implementing functionality described as being carried out by one or more components discussed above or instructions for implementing one or more of the methods described above. The processor 702 may access the memory 704 by way of a system bus 706. In addition to storing executable instructions, the memory 704 may also store a collaborative summary, a care plan, etc.

The computing device 700 additionally includes a data store 708 that is accessible by the processor 702 by way of the system bus 706. The data store 708 may include executable instructions, care plan data, etc. The computing device 700 also includes an input interface 710 that allows external devices to communicate with the computing device 700. For instance, the input interface 710 may be used to receive instructions from an external computer device, from a user, etc. The computing device 700 also includes an output interface 712 that interfaces the computing device 700 with one or more external devices. For example, the computing device 700 may display text, images, etc. by way of the output interface 712.

It is contemplated that the external devices that communicate with the computing device 700 via the input interface 710 and the output interface 712 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 700 in a manner free from constraints imposed by input device such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 700 may be a distributed system. Thus, for instance, several devices may be in communication by way of a network connection and may collectively perform tasks described as being performed by the computing device 700.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and Blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A server computing device comprising:
   a processor; and
   memory storing a care plan application, wherein the care plan application is configured to facilitate creation, distribution, and maintenance of a care plan for a patient, wherein the care plan application, when executed by the processor, is configured to perform acts comprising:
   receiving a request from a first client computing device for the care plan for the patient, wherein the first client computing device is operated by a first clinician who is partaking in the care plan for the patient, and further wherein multiple clinicians from different healthcare organizations partake in the care plan for the patient, with each clinician in the multiple clinicians having a role specified in the care plan that is different from roles of other clinicians partaking in the care plan for the patient;

responsive to receiving the request, retrieving the care plan for the patient from a data repository, wherein the care plan for the patient comprises a collaborative summary for the patient that was collaboratively constructed by the multiple clinicians with respect to care provided to the patient in accordance with the care plan for the patient;

transmitting the care plan for the patient to the first client computing device for display in a graphical user interface (GUI) of the care plan application on a display of the first client computing device, wherein upon a button corresponding to the collaborative summary for the patient being selected in the GUI of the care plan application, an editable collaborative summary text field is presented in the GUI of the care plan application, wherein the editable collaborative summary text field comprises the collaborative summary is for the patient;

receiving an updated collaborative summary from the first client computing device, wherein the updated collaborative summary comprises an alteration made to the collaborative summary by the first clinician by way of the editable collaborative summary text field; and subsequent to receiving the updated collaborative summary, transmitting the updated collaborative summary to a second client computing device that is operated by a second clinician in the multiple clinicians partaking in the care plan for the patient upon receiving a request for the care plan for the patient from the second client computing device, wherein the updated collaborative summary is displayed in the editable collaborative summary text field in the GUI of the care plan application.

2. The server computing device of claim 1, wherein the collaborative summary comprises a first update made by the second clinician and a second update made by a third clinician partaking in the care plan for the patient, and further when the collaborative summary, when displayed in the editable collaborative summary text field, depicts that the first clinician made the first update and the second clinician made the second update.

3. The server computing device of claim 1, wherein the collaborative summary, when displayed in the editable collaborative summary text field on the display of the first client computing device, depicts identities of the multiple clinicians, and further wherein updates to the collaborative summary made by a third clinician in the multiple clinicians is displayed responsive to an identity of the third clinician in the multiple clinicians being selected.

4. The server computing device of claim 1, wherein the request is received responsive to the first clinician selecting a button on the GUI of the care plan application presented on the display.

5. The server computing device of claim 1, wherein the request is received responsive to the clinician selecting an identity of the patient on the GUI of the care plan application.

6. The server computing device of claim 1, wherein the collaborative summary, when displayed in the editable collaborative summary text field on the display of the first client computing device, depicts times when clinicians in the multiple clinicians updated the collaborative summary.

7. A method executed by a server computing device that is in network communication with a plurality of client computing devices, the method comprising:

receiving, from a care plan application executing on a first client computing device in the client computing devices, a request for a care plan for a patient, wherein multiple clinicians partake in the care plan for the patient, the first client computing device operated by a first clinician in the multiple clinicians, and further wherein the collaborative summary comprises portions that where respectively received from computing devices operated by clinicians in the multiple clinicians;

responsive to receiving the request, retrieving the care plan for the patient from a data repository;

responsive to retrieving the care plan for the patient from the data repository, transmitting the care plan for the patient to the first client computing device for display in a graphical user interface (GUI) of the care plan application, wherein upon a button corresponding to the collaborative summary for the patient being selected in the GUI of the care plan application, an editable collaborative summary text field is presented in the GUI of the care plan application, wherein the freeform text is editable by the clinician by way of the editable collaborative summary text field;

receiving an updated collaborative summary from the first client computing device, wherein the updated collaborative summary comprises an alteration made to the collaborative summary by the first clinician by way of the editable collaborative summary text field; and subsequent to receiving the updated collaborative summary, transmitting the updated collaborative summary to a second client computing device that is operated by a second clinician in the multiple clinicians partaking in the care plan for the patient upon receiving a request for the care plan for the patient from the second client computing device, wherein the updated collaborative summary is displayed in the editable collaborative summary text field in the GUI of the care plan application at the second client computing device.

8. The method of claim 7, wherein the collaborative summary, when displayed on the display of the first client computing device in the GUI of the care plan application, depicts a history of updates made to the collaborative summary.

9. The method of claim 7, wherein the collaborative summary, when displayed on the display of the client computing device in the GUI of the care plan application, depicts identities of the multiple clinicians, and further wherein updates to the collaborative summary made by a third clinician in the multiple clinicians is displayed responsive to an identity of the third clinician in the multiple clinicians being selected in the GUI of the care plan application.

10. The method of claim 7, wherein the request is received responsive to the first clinician selecting a button on the GUI of the care plan application presented on the display of the first client computing device.

11. The method of claim 7, wherein the request is received responsive to the first clinician selecting an identity of the patient on the GUI of the care plan application.

12. The method of claim 7, wherein the collaborative summary, when displayed on the display of the first client computing device, depicts times when clinicians in the multiple clinicians updated the collaborative summary.

13. A computer-readable storage medium comprising a care plan application, wherein the care plan application, when executed by a processor, causes the processor to perform acts comprising:

receiving a request from a first client computing device for the care plan for the patient, wherein the first client computing device is operated by a first clinician who is partaking in the care plan for the patient, and further wherein multiple clinicians from different healthcare organizations partake in the care plan for the patient, with each clinician in the multiple clinicians having a role specified in the care plan that is different from roles of other clinicians partaking in the care plan for the patient;

responsive to receiving the request, retrieving the care plan for the patient from a data repository, wherein the care plan for the patient comprises a collaborative summary for the patient that was collaboratively constructed by the multiple clinicians with respect to care provided to the patient in accordance with the care plan for the patient; and transmitting the care plan for the patient to the first client computing device for display in a graphical user interface (GUI) of the care plan application on a display of the first client computing device, wherein upon a button corresponding to the collaborative summary for the patient being selected in the GUI of the care plan application, an editable collaborative summary text field is presented in the GUI of the care plan application, wherein the editable collaborative summary text field comprises the collaborative summary for the patient;

receiving an updated collaborative summary from the first client computing device, wherein the updated collaborative summary comprises an alteration made to the collaborative summary by the first clinician by way of the editable collaborative summary text field; and subsequent to receiving the updated collaborative summary, transmitting the updated collaborative summary to a second client computing device that is operated by a second clinician in the multiple clinicians partaking in the care plan for the patient upon receiving a request for the care plan for the patient from the second client computing device, wherein the updated collaborative summary is displayed in the editable collaborative summary text field in the GUI of the care plan application.

14. The computer-readable storage medium of claim 13, wherein the collaborative summary comprises a first update made by the second clinician and a second update made by a third clinician partaking in the care plan for the patient, and further when the collaborative summary, when displayed in the editable collaborative summary text field, depicts that the first clinician made the first update and the second clinician made the second update.

15. The computer-readable storage medium of claim 14, wherein the collaborative summary, when displayed in the editable collaborative summary text field on the display of the first client computing device, depicts identities of the multiple clinicians, and further wherein updates to the collaborative summary made by a third clinician in the multiple clinicians is displayed responsive to an identity of the third clinician in the multiple clinicians being selected.

16. The computer-readable storage medium of claim 14, wherein the request is received responsive to the first clinician selecting a button on the GUI of the care plan application presented on the display.

17. The computer-readable storage medium of claim 14, wherein the request is received responsive to the clinician selecting an identity of the patient on the GUI of the care plan application.

18. The computer-readable storage medium of claim 14, wherein the collaborative summary, when displayed in the editable collaborative summary text field on the display of the first client computing device, depicts times when clinicians in the multiple clinicians updated the collaborative summary.

\* \* \* \* \*